United States Patent [19]
Shkarlet

[11] 3,963,980
[45] June 15, 1976

[54] ULTRASONIC INSTRUMENT FOR NON-DESTRUCTIVE TESTING OF ARTICLES WITH CURRENT-CONDUCTING SURFACE

[76] Inventor: Jury Mikhailovich Shkarlet, Lefortovsky val, 12, kv. 40, Moscow, U.S.S.R.

[22] Filed: Aug. 29, 1973

[21] Appl. No.: 392,789

[52] U.S. Cl. .................................................. 324/40
[51] Int. Cl.² .......................................... G01R 33/14
[58] Field of Search ........................... 324/40, 34 R

[56] References Cited
UNITED STATES PATENTS

| | | | |
|---|---|---|---|
| 2,467,306 | 4/1949 | Habig | 324/40 |
| 3,361,960 | 6/1968 | Renken, Jr. et al. | 324/40 |

FOREIGN PATENTS OR APPLICATIONS

| | | | |
|---|---|---|---|
| 11,404 | 5/1969 | Japan | 324/40 |
| 991,890 | 5/1965 | United Kingdom | 324/40 |
| 594,158 | 11/1947 | United Kingdom | 324/40 |
| 219,218 | 3/1969 | U.S.S.R. | 324/40 |

OTHER PUBLICATIONS

Owston, A High Frequency Eddy–Current Non-Destructive Testing Apparatus with Automatic Probe Positioning Suitable for Scanning Applications, Journal of Physics E, Oct. 1970, pp. 814–818.

Kim et al., Flux Concentrator for High-Intensity Pulsed Magnetic Fields, The Review of Scientific Instruments, July 1959, pp. 524–533.

Howland et al., Flux Concentration by Stationary Conductors, Proceedings of the International Conference on High Magnetic Fields, 1961, pp. 249–257.

Primary Examiner—Stanley T. Krawczewicz
Attorney, Agent, or Firm—Haseltine, Lake & Waters

[57] ABSTRACT

An instrument comprising a generator feeding an electromagnetoacoustic transducer whose signals are applied to recording system.

The transducer has at least one inductance coil; arranged between the latter and an article being tested is a member with a current-conducting surface making up a closed loop, one portion thereof is inductively connected to the coil, where as the other portion is arranged close to the surface of the article being tested. Said member is made of a durable material in order to protect the coil from mechanical damage.

8 Claims, 8 Drawing Figures

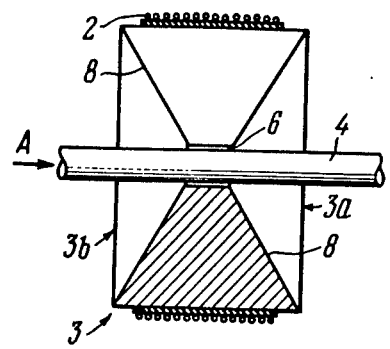
FIG. 2
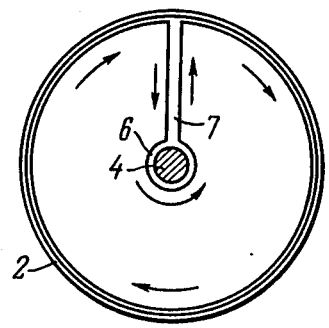
FIG. 3
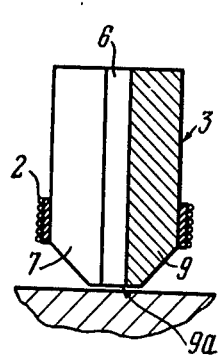
FIG. 5
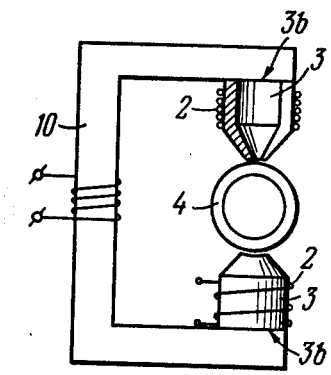
FIG. 6
FIG. 7
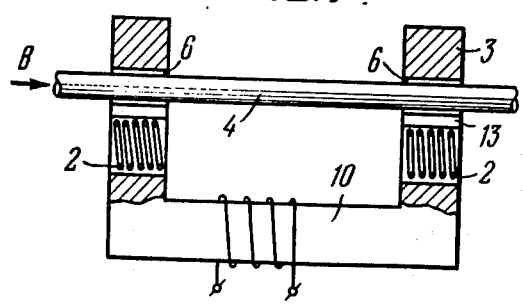
FIG. 8
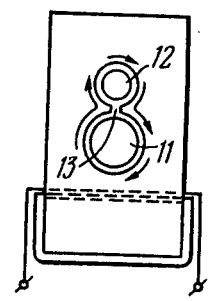

ULTRASONIC INSTRUMENT FOR NON-DESTRUCTIVE TESTING OF ARTICLES WITH CURRENT-CONDUCTING SURFACE

The present invention relates to means for quality control of materials and articles and more particularly to an instrument for non-destructive testing of articles with a current-conducting surface.

The invention may be used with the greatest advantage for flaw detection and measuring the thickness of articles.

One of the commonest methods of non-destructive testing is the ultrasonic method which consists of generating ultrasonic oscillations in an article being tested and registering oscillations passing through the article or reflected from the surface thereof.

Generation of ultrasonic oscillations and reception of useful signals is done by piezoelectric transducers which must be in acoustic contact with the surface of an article being tested.

The above requirement limits the sphere of application of this method, as it makes impossible quality control of fast-moving articles directly in the course of manufacturing thereof.

Free of the above disadvantages is the electromagnetoacoustic method which ensures contactless generation and reception of ultrasonic oscillations.

Generation of ultrasonic oscillations in an article being tested is effected through interaction of a high-frequency electromagnetic field generated by a coil placed close to the surface of the article being tested with a magnetic field.

Reception of ultrasonic oscillations is effected by inducing an electromotive force either in the same or in another inductance coil in the zone of action of the magnetic field.

This method is the most promising for high-rate quality control of articles, including those in a hot state.

In the prior art, there are instruments for testing articles with a current-conducting surface, comprising a generator supplying current pulses to an electromagnetoacoustic transducer having at least one inductance coil, an article being tested placed in the zone of action thereof, and also comprising a recording system, applied whereto are signals from said transducer.

A disadvantage of such instruments resides in their relatively low reliability due to the necessity of the inductance coil being as close to an article being tested as possible, which, under the conditions of flow-line quality control, may lead to the inductance coil being damaged as a result of accidental contacts thereof with the article being tested.

Protection of inductance coils from damage is effected in the above instruments by placing these coils at a certain distance from an article being tested, or by introducing additional packings between the inductance coil and an article being tested, which results in a lower sensitivity of the instrument.

It is an object of the present invention to provide an instrument for non-destructive testing of articles with a current-conducting surface, comprising such an electroacoustic transducer which would ensure high sensitivity of the instrument in checking articles of different shapes, including flowline checking, and also being sufficiently reliable in operation.

This and other objects are attained according to the invention, by placing between the inductance coil and an article being tested a member with a current-conducting surface making up a closed loop, one portion thereof is inductively connected to the inductance coil and the other is placed close to the surface of the article being tested, said member being made of a mechanically durable material in order to protect the coil from mechanical damage.

The foresaid solution makes it possible to raise the reliability of the instrument as a result of protecting the inductance coil from mechanical damage with the aid of the member with a current-conducting surface whose mechanical strength is higher than that of the coil, this being attained without any tangible decrease in the effectiveness of the electromagnetoacoustic transducer.

One of practicable alternative embodiments of the invention comprises a magnet, whereas the member with a current-conducting surface is made of a ferromagnetic material and is connected to at least one of the poles of said magnet.

The aforesaid embodiment is advisable in cases when the checking conditions necessitate a high rate of repetition of driving pulses, for example, at a high speed of movement of an article being tested and with great density of points (areas) to be tested.

In both versions of the instrument, according to the invention, the member with a current-conducting surface may be in the form of a cylinder, with its current-conducting surface being formed by the lateral surface of said cylinder coiled around which is an inductance coil, whereas in the zone of the winding thereof there is a channel opened at least at one end face of the cylinder and connected with the lateral surface thereof by a longitudinal slot.

The above structure of the member simplifies to the utmost the manufacturing thereof, minimizes electric losses and also makes it possible to produce a high-frequency electromagnetic field and a magnetizing pulsed field close to the surface of an article being tested.

In another version of the instrument, the end face of the cylinder, to which the channel opens, faces an article being tested, with the surface of that end face being equidistant with respect to the surface of the article being tested.

The above structure is advisable in checking flat articles for example, sheets, or articles with a great radius of curvature, for example, large-diameter pipes.

It is expedient that the end of the cylinder on the side of an article being tested be reduced to a truncated cone, with the smaller base thereof facing the article being tested.

This makes it possible to localize the checking zone of flat articles or of those with a great radius of curvature.

In still another version of the instrument, the channel may be opened at both ends, with the other end thereof opening through the lateral surface of the cylinder, whereas the second end face of the cylinder may be used for fastening thereof.

This is advisable in cases when the opposite end face of the cylinder, for reasons of the design, has to be fastened to a body made of a current-conducting material and is meant to raise the effectiveness of the electromagnetoacoustic transducer due to currents induced in the current-conducting surface of the cylinder, predominantly over the end face surface thereof placed close to which is an article being tested.

The channel in the cylinder may be through, i.e. opened at both end faces of the cylinder and designed for placing in it an article being tested, the surface of the channel having to be equidistant with respect to the surface of the article being tested.

This makes it possible to carry out flow-line checking of longitudinal articles, such as rods, pipes, etc., by way of passing them through the channel of the cylinder which is open on both sides.

It is expedient that at least one of the end faces of the cylinder with a through channel be provided with an inner axial recess to reduce the length of the channel relative to that of the generatrix of the surface of the cylinder.

This makes it possible to localize checking of longitudinal articles without reducing the effectiveness of the electromagnetoacoustic transducer.

According to yet another practicable version of the instrument, the member with a current-conducting surface is provided with two openings communicating with each other, placed in one thereof is an inductance coil, whereas placed in the other is an article being tested.

This is advisable in cases when in the course of operation some accidental mechanical damage may be inflicted upon the inductance coil even if it is placed at a substantial distance from an article being tested. The inductance coil, therefore, may be placed inside said member, namely, in one of the communicating openings, whereas an article being tested is placed in the electromagnetic field of the current through the surface of the second opening.

The invention will hereinafter be explained in greater detail with reference to preferred embodiments thereof taken in conjunction with the accompanying drawings, wherein:

FIG. 2 is a longitudinal section of an electromagnetoacoustic transducer of the passage type;

FIG. 3 is a view along Arrow A of FIG. 2;

FIG. 5 is a longitudinal section of an electromagnetoacoustic transducer with a through channel;

FIG. 6 is a longitudinal section of an electromagnetoacoustic transducer with a magnet;

FIG. 7 is a view of an electromagnetoacoustic transducer with two passage openings (with a partial longitudinal section FIG. 8 is a view along Arrow B of FIG. 7.

Figure 1:
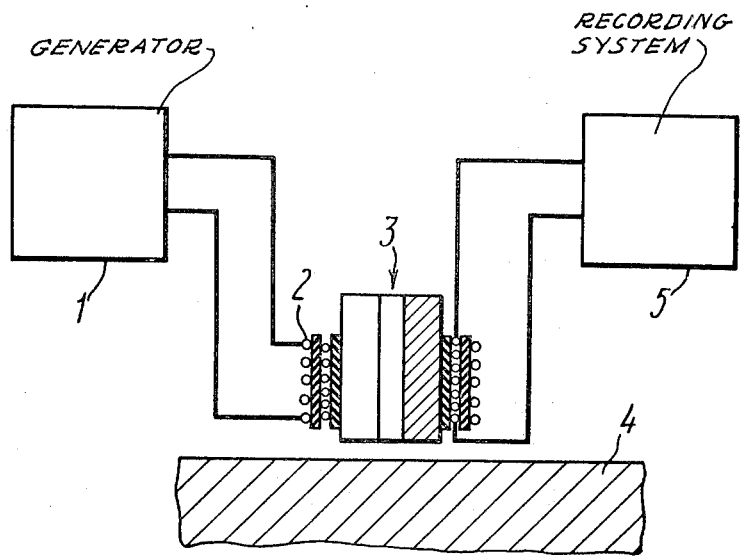
FIG. 1 is a diagram of an ultrasonic instrument for nondestructive testing of articles with a current-conducting surface (with a longitudinal section of an electromagneticacoustic transducer of the superimposed type)

The proposed ultrasonic instrument for non-destructive testing of articles with a current-conducting surface comprises a generator 1 (FIG. 1) which is connected to an electromagnetoacoustic transducer designed as an inductance coil 2 wound, according to the invention, upon a portion of a member 3 with a current-conducting surface making up a closed loop, part thereof is inductively connected to the coil 2. The coil 2 is mounted upon the member 3 in such a way that at least part of the surface of the member 3 is placed between an article 4 being tested and the coil 2 and protects the latter from mechanical damage, for which purpose the member 3 is made of a mechanically durable material, for example, copper. The inductance coil 2 is connected to an input of a recording system 5.

In one embodiment of the present invention, the member 3 is in the form of a cylinder (as is shown in FIGS. 1 through 6), wound upon the lateral surface thereof is the inductance coil 2, whereas provided in the cylindrical member 3, in the zone where the inductance coil is wound, are a channel 6 and a longitudinal radial slot 7 which communicates the channel 6 with the lateral surface of the member 3.

Figure 4:
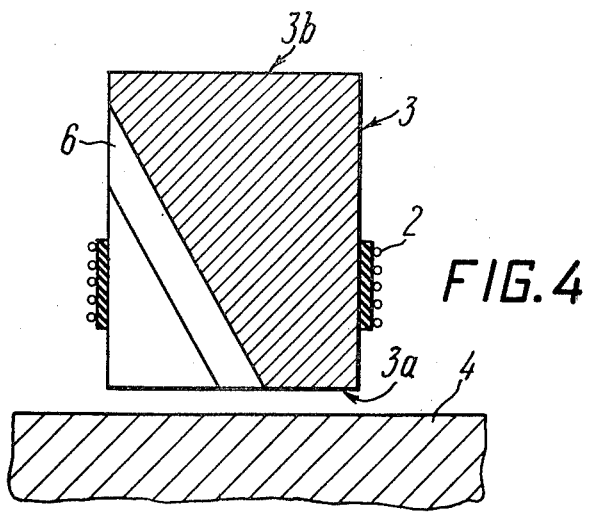
FIG. 4 is a longitudinal section of an electromagnetoacoustic transducer with a slanted through channel.

The channel 6 may be both axial and through (FIGS. 1–3, 5 and 6), as well as slanted, with at least one of its ends opened at the lateral surface of the cylinder 3 (FIG. 4).

The article 4 being tested may be placed both near an end face 3a of the cylinder 3, opening whereto is the channel 6 (as is shown in FIGS. 1, 4, 5 and 6), and in the channel 6 itself (FIG. 2).

In all possible mutual positions of the member 3 and the article 4 being tested, the portion of the current-conducting surface of the member 3 facing the article 4 being tested must be as equidistant as possible to the surface thereof.

If the article 4 is placed in the through axial channel 6 which opens at both end faces, 3a and 3b, of the cylinder 3, provision may be made at one or both end faces, 3a and 3b, of the member 3 for inner recesses 8 (FIG. 2), for example, conical, in order to reduce the length of the channel 6 relative to that of the generatirx of the outer surface of the cylinder 3.

If the article 4 is placed near an end face of the cylindrical member 3, said end face may be reduced to a truncated cone 9 (FIGS. 5 and 6), with the smaller base 9a thereof facing the article 4 being tested.

The member 3 may be made of a ferromagnetic material, in which case the instrument is to be provided with an electromagnet 10 (FIGS. 6–8) or a permanent magnet, the member 3 being connected to the poles thereof.

In another embodiment of the present invention, the member 3 is U-shaped and has two pairs of coaxial openings 11 and 12, the openings in each pair being in communication via a radial slot 13.

Arranged in each of the lower openings 11 is the inductance coil 2, whereas the upper openings 12 are designed for the passage through them of the article 4 being tested, which is made of a ferromagnetic metal, for example, steel.

The proposed ultrasonic instrument for non-destructive testing of articles with a current conducting surface operates as follows.

The generator 1 generates high-frequency current pulses which are applied to the inductance coil 2 of the electromagnetoacoustic transducer.

As this takes place, the portion of the current-conducting surface of the member 3, which is found close to the coil 2, performs the function of a secondary winding of a transformer, the function of the primary winding thereof being performed by the inductance coil 2 itself.

The load of this transformer is the portion of the current-conducting surface of the member 3, arranged close to the surface of the article 4 being tested.

High-frequency current, applied from the generator 1 to the inductance coil 2, induces secondary current of the same frequency in the surface of the member 3 and, flowing across the portion of the surface of the member 3 disposed close to the surface of the article 4 being tested, produces a high-frequency electromagnetic field near that surface.

The latter field induces in the surface layer of the article 4 under the member 3 eddy currents, whose interaction with the magnetizing magnetic field in this portion of the surface of the article 4 produces (due to the electrodynamic effect in current-conducting bodies or due to the magnetostrictive effect) ultrasonic oscillations whose frequency is equal to that of the current supplied from the generator 1 to the coil 2.

The source of the magnetizing field may be either the same or another coil mounted upon the member 3, applied to which from the generator 1, simultaneously with the high-frequency current pulse, is a pulse of a substantially greater duration than the high-frequency pulse.

A permanent magnet or the electromagnet 10 can also be used as a source of the magnetizing field.

In this case, making the member 3 of a ferromagnetic material makes it possible to reduce the magnetic resistance of the "magnetic circuit — article being tested" circuit. This may lead to a maximum reduction in the period of exciting and receiving ultrasonic oscillations and ensure a high rate of repetition of the sounding process.

Although the member 3 may, generally, be of any shape, making it in the form of a cylinder is the most effective technologically.

With the channel 6 opened at one end face of the cylinder 3 and the longitudinal slot 7 communicating the surface of the channel 6 with the lateral surface of the cylinder 3, currents induced by the inductance coil 2 in the surface of the cylinder 3 flow across the portion thereof disposed in immediate proximity to the surface of the article 4 being tested.

This produces a high-frequency electromagnetic field and a magnetizing pulse field near the surface of the article-being tested.

The electromagnetic field is produced in a similar manner in the case when the member 3 has two openings, 11 and 12. As the article 4 being tested enters the through channel 6, it is desirable that the surfaces of the channel 6 and the article 4 being tested be equidistant.

This makes it possible to raise the effectiveness of the electromagnetoacoustic transducer due to an increase in the activity coefficient.

If the article 4 being tested is arranged near an end face of the cylinder 3, it is desirable that the surface of the end face 3a and that of the article 4 being tested be equidistant in order to ensure a uniform gap between the electromagnetoacoustic transducer and the surface of the article 4 being tested so as to reduce power losses of the electromagnetic field in that gap.

In cases when the member 3 is secured to a current-conducting body, for example, to the casing of the electromagnetoacoustic transducer, it is advisable that the channel 6 be slanted in order to ensure the currents induced in the surface of the cylinder 3 flowing predominantly across the portion of that surface found close to the article 4 being tested, which means raising the efficiency of the electromagnetoacoustic transducer The provision in the cylindrical member 3 of the recess 8 in the form of the truncated cone 9 reduces the area of the surface of the cylinder 3 near the surface of the article 4 being tested, which makes the currents induced by the coil 2 in the surface of the cylinder 3 flow across a limited area, i.e. localizes the checking zone.

In the course of receiving ultrasonic pulses, inverse effects produce an electromagnetic field pulse in the gap between the article 4 being tested and the member 3, which induces current in the current-conducting surface layer of the member 3. That current, in turn, induces an electromotive force in the inductance coil 2 or in another coil disposed close to the surface of the member 3, the signal being applied to the recording system 5 of the known design, which is provided with means for signal amplification and processing.

What is claimed is:

1. An ultrasonic instrument for non-destructive testing of articles with a current-conducting surface, comprising: a generator generating current pulses; an electromagnetoacoustic transducer connected to said generator and having at least one inductance coil; a member with a current-conducting surface making up a closed loop, arranged between the inductance coil of said transducer and an article being tested in such a way that one portion of said surface of that member is inductively connected to said inductance coil and the other is arranged close to the surface of the article being tested; said member being made of a mechanically durable material in order to protect said inductance coil from mechanical damage; a recording system connected to said transducer and receiving signals from it, the member with a current-conducting surface being in the form of a cylinder, with the current-conducting surface thereof being formed by the lateral surface of that cylinder wound upon which is an inductance coil and by a channel provided in the zone of the winding of that coil which is opened at least at one of the end faces of the cylinder and communicates with the lateral surface thereof by means of a longitudinal slot.

2. An instrument as claimed in claim 1, having a magnet, whereas the member is made of a ferromagnetic material and connected to at least one pole of said magnet.

3. An instrument as claimed in claim 1, wherein the end face of the cylinder, at which the channel opens, faces an article being tested, whereas the surface of the end face is equidistant relative to the surface of the article being tested.

4. An instrument as claimed in claim 3, wherein the end face of the cylinder on the side of an article being tested is reduced to a truncated cone, the smaller base of that cone facing the article being tested.

5. An instrument as claimed in claim 3, wherein the channel is through, with the second end thereof opening at the lateral surface of the cylinder, the other end face serving for fastening thereof.

6. An instrument as claimed in claim 1, wherein the channel is through, opens at both ends of the cylinder and is designed for an article being tested to be placed inside it, with the surface of that channel being equidistant relative to that of the article being tested 7. An instrument as claimed in claim 6, wherein at least one of the end faces of the cylinder is provided with an inner recess which reduces the length of the channel, as compared to that of the generatrix of the surface of the cylinder.

8. An instrument as claimed in claim 1, wherein the member with a current-conducting surface is provided with two communicating openings, with the inductance coil disposed in one thereof, whereas the other is designed for an article being tested to be placed either in it or near it.

* * * * *